US008504514B2

(12) United States Patent
Fortier et al.

(10) Patent No.: US 8,504,514 B2
(45) Date of Patent: *Aug. 6, 2013

(54) ADAPTIVE HYBRID REASONING DECISION SUPPORT SYSTEM

(75) Inventors: Paul J. Fortier, Portsmouth, RI (US); Theophano Mitsa, Melrose, MA (US); Nancy Dluhy, Portsmouth, RI (US)

(73) Assignee: University of Massachusetts, Shrewsbury, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/584,380

(22) Filed: Aug. 13, 2012

(65) Prior Publication Data
US 2012/0310947 A1      Dec. 6, 2012

Related U.S. Application Data

(63) Continuation of application No. 12/435,944, filed on May 5, 2009, now Pat. No. 8,244,733.

(60) Provisional application No. 61/050,419, filed on May 5, 2008.

(51) Int. Cl.
*G06F 7/00* (2006.01)
*G06F 17/00* (2006.01)

(52) U.S. Cl.
USPC ............ 707/603; 707/705; 707/736; 707/741

(58) Field of Classification Search
USPC ................. 707/603, 705, 736, 741, 999.1
See application file for complete search history.

(56) References Cited

U.S. PATENT DOCUMENTS

| 6,807,537 | B1 * | 10/2004 | Thiesson et al. | 706/52 |
| 7,809,709 | B1 * | 10/2010 | Harrison, Jr. | 707/707 |
| 7,836,060 | B1 | 11/2010 | Rennison | |
| 7,941,431 | B2 * | 5/2011 | Bluhm et al. | 707/736 |
| 7,943,431 | B2 | 5/2011 | San Antonio et al. | |
| 8,244,733 | B2 | 8/2012 | Fortier et al. | |
| 2002/0094088 | A1 * | 7/2002 | Okaue | 380/278 |
| 2003/0018626 | A1 * | 1/2003 | Kay et al. | 707/3 |
| 2005/0169179 | A1 * | 8/2005 | Antal et al. | 370/231 |
| 2006/0095524 | A1 * | 5/2006 | Kay et al. | 709/206 |

(Continued)

OTHER PUBLICATIONS

Aamodt, A., "Case-Based Reasoning Foundation Issues, Methodological Variations, and Systems Approaches", AI Communications, vol. 7, No. 1, pp. 39-59, 1994.

(Continued)

*Primary Examiner* — Hares Jami
(74) *Attorney, Agent, or Firm* — Lando & Anastasi, LLP

(57) ABSTRACT

A method for indexing a plurality of nodes using a computer system is provided. The computer system includes data storage and a processor coupled to the data storage. The method includes acts of storing the plurality of nodes in the data storage, each of the plurality of nodes having a hit count, a link count and an outcome, creating a qualitative index ordering a plurality of nodes according to the hit count, the link count and the outcome of each node and storing the qualitative index in the data storage. The hit count of each node indicates a number of times a case attribute associated with the node is presented to a user. The link count of each node indicates a number of times the case attribute associated with the node is affirmed as useful. The outcome of each node indicates a desirability of the outcome.

15 Claims, 7 Drawing Sheets

U.S. PATENT DOCUMENTS

| | | |
|---|---|---|
| 2007/0156677 A1 | 7/2007 | Szabo |
| 2007/0185868 A1* | 8/2007 | Roth et al. .................... 707/6 |
| 2009/0089277 A1 | 4/2009 | Cheslow |
| 2009/0132561 A1 | 5/2009 | Cormode et al. |
| 2009/0172603 A1 | 7/2009 | Young Suk Lee |
| 2010/0070448 A1 | 3/2010 | Omoigui |
| 2010/0205179 A1* | 8/2010 | Carson et al. ............... 707/740 |

OTHER PUBLICATIONS

Aha, D. et al., "Case-Based Reasoning Integrations: Papers from the 1998 AAAI Workshop", Technical Report WS-98-15, AAAI Press, 1998. Bichindaritz, I., et al., pp. 22-38.

Allemang, D., "Combining Case-Based Reasoning and Task-Specific Architectures", IEEE Expert, Oct. 1994, pp. 24-34.

Althoff, K. et al., "INRECA-A Seamless Integration of Inducation and Case-Based Reasoning for Decision-Support Trees", Proceedings of the Eight Workshop German SIG on Machine Learning, 1995.

Avramenko et al., "Case-Based Reasoning Approach", SpringerLink, 2007, pp. 51-70. Download:http://www.springerlink.com/content/w1m23460867t8513/fulltext.pdf.

Bakken, S., "Chapter 9 Informatics for Patient Safety: A Nursing Research Perspective", Annual Review of Nursing Research, (24) pp. 219-254, 2006.

Barnett, G. et al., "DXplain on the internet", Proc. AMA symposium, pp. 607-611. 1998.

Beard, N., MD, et al., "Standards-Based Sharable Active Guideline Environment (SAGE): A Project to Develop a Universal Framework for Encoding and Disseminating Electronic Clinical Practice Guidelines", Proc. AMIA Symposium, pp. 973, 2002.

Bemmel J. et al., Handbook of Medical Informatics, Berlin, Germany, Springer, 2002.

Berner, E.S., Clinical Decision Support Systems: Theory and Practice, Berlin, Germany, Springer, 1998.

Branting, L.K., "Reasoning with Rules and Precedents", Kluwer Academic Publishers, 1999.

Casanova, A. et al., Reasoning with Cases in Clinical Problem Solving, IEEE, Int'l Conference on Systems, Man, Cybernetics, Oct. 22-25, 1995, (3) pp. 1986-1990.

Chang, B., et al., "CANDI A Knowledge-based System for Nursing Diagnosis", Computers in Nursing, Jan./Feb. 1988, vol. 6:1, pp. 13-21.

Chi, R. et al., "An Integrated Approach of Rule-Based and Case-Based Reasoning for Decision Support", ACM Annual Computer Science Conference, pp. 255-267, 1999.

deDombal, F.T., et al, "Human and Computer-aided Diagnosis of Abdominal Pain: Further Report with Emphasis on Performance of Clinicians", British Medical Journal, (1) Mar. 1974, pp. 376-380.

Domingos, P., "Unifying Instance-Based and Rule-Based Induction", Machine Learning, (24) 1996, p. 141-168.

Fortier, N. "Theory Synthesis: The Synthesized Model of Symptom Experience", TRxxx-NUR-2006, University of Massachusetts, Dartmouth. 2006.

Fox, J. et al., "Decision Support and Disease Management: A Logic Engineering Approach", IEEE Transactions on Information Technology in Biomedicine, (2) 4, Dec. 1998, pp. 217-228.

Golding, A.R. et al. "Pronouncing Names by a Combination of Case-Based and Rule-Based Reasoning", doctoral dissertation, Stanford University. 1991.

Golding, A.R., et al., "Improving Accuracy by a Combining Rule-Based and Case-Based Reasoning", Artificial Intelligence, (87) 1996, pp. 215-254.

Hajioff, S., "Computerized Decision Support Systems: an Overview", Health Informatics Journal (4), pp. 23-28, 1998.

Han, J., et al., "Mining Frequent Patterns without Candidate Generation", 2000 ACM SIGMOD Int'l conference on Management of Data, pp. 1-12. 2000.

Huei-Pi, C., et al., Case Match Reduction Through the Integration of Rule-Based and Case-Based Reasoning Procedures, Newcastle Business School, University of Northumbria at New Castle, pp. 33-38.

Koch, B. et al., "EXTEND: A Prototype Expert System for Teaching Nursing Diagnosis", Computers in Nursing (11)1, pp. 35-41, 1993.

Koch, B., "Development, Validation, and Evaluation of an Expert System to Provide Decision Support for Nursing diagnosis in Nursing Care", ITCH Conference Proceedings, pp. 309-313, 1996.

Koton, P., "Reasoning about Evidence in Causal Explanations", Proceedings of the AAAI-88, AAAI Press, 1988.

Leake, D.B., "Combining Rules and Cases to Learn Case Adaptation", Proceedings of the 17th Annual Conference of the Cognitive Science, 1995.

Lopez and Plaza, "Case-based Planning for Medical Diagnosis", Methodologies for Intelligent Systems 7th Intern. Symp., ISMIS'93, pp. 96-105, Springer, 1993.

Marling, C.R. et al., "Integrating Case-Based and Rule-Based Reasoning to Meet Multiple Design Constraints", Computational Intelligence, vol. 15, pp. 308-322, 1999.

Musen, M.A., "Stanford Medical Informatics: Uncommon Research, Common Goals", MD Comput. (16)1, pp. 47-48, 1999.

Myers, J.D., "The Background of INTERNIST-I and QMR", in a History of Medical Informatics, eds. B.I. Blum and K. Duncan, pp. 427-433, New York, NY: ACM Press, 1990.

O'Neill, E., PhD., RN, "Knowledge Acquisition, Synthesis, and Validation: A Model for Decision Support Systems", Methodological Issues in Nursing Research, Journal of Advanced Nursing, 47(2), Dec. 2004, pp. 134-142.

Prentzas, J. et al., "Integrating Hybrid Rule-Based with Case-Based Reasoning", S. Craw and A. Preece (Eds.) ECCBHR 2002, LNA1 2416, pp. 336-349, Springer-Verlag, Berlin-Heidelberg, 2002.

Ram, Ashwin, "Indexing, Elaboration and Refinement: Incremental Learning of Explanatory Cases", Machine Learning, 10, 201-248, 1993.

Rissland, E. et al., "Combining Case-Based and Rule-Based Reasoning: A Heuristic Approach", IJCAI, pp. 524-530, 1989.

Roth, K., et al., "CANDI Development of the Automated Nursing Assessment Tool", Computers in Nursing, Sep./Oct. 1989, (7) 5, pp. 222-227.

Scott et al., "Knowledge-Driven Multidimensional Indexing Structure for Biomedical Media Database Retrieval", IEEE, May 2007, pp. 320-331. Download: http://ieeexplore.ieee.org/stamp/stamp.jsp?arnumber=04167901.

Shortliffe, H., Computer-Based Medical Consultations: MYCIN, Elsevier Computer Science Library, Artificial Intelligence Series, New York, NY: Elsevier, 1976.

Shortliffe, H., et al., "ONCOCIN: An Expert System for Oncology Protocol Management", Seventh International Joint Conference on Artificial Intelligence, Vancouver, BC. 1981.

Sim, I. et al., "Clinical Decision Support Systems for the Practice of Evidence-Based Medicine", JAMIA (8)6, pp. 527-534, 2001.

Surma, J. et al., "An Empirical Study on Combining Instance-Based and Rule-Based Classifier, Case-Based Reasoning Research and Develop;ment", Proceedings of the First International Conference, ICCBR-95. Lectures Notes in Computer Science, vol. 1010,Springer-Vertag, Berlin Heidelberg, New York, 1995.

Teich, J.M. et al., "Clinical Decision Support in Electronic Prescribing: Recommendations and an Action Plan", JAMIA (12)4, pp. 365-376, 2005.

Teich, J.M. et al., "Clinical Decision Support Systems Come of Age", MD Comput. (17)1, pp. 43-46, 2000.

Watson, I. et al., "Case-Based Reasoning: A Review", Knowledge Engineering Review, vol. 9:4, pp. 327-354, 1994.

Zielstorff, R.D. et al., "Evaluation of a Decision Support System for Pressure Ulcer Prevention and Management: Preliminary Findings", AMIA Annual Symposium Proceedings, pp. 248-252, 1997.

* cited by examiner

ADAPTIVE HYBRID REASONING DECISION SUPPORT SYSTEM

RELATED APPLICATIONS

This application is a continuation of and also claims priority under 35 U.S.C. §120 to U.S. patent application Ser. No. 12/435,944, which was filed on May 5, 2009. U.S. patent application Ser. No. 12/435,944 claims priority under 35 U.S.C. §119(e) to U.S. Provisional Application Ser. No. 61/050,419, entitled "Adaptive Hybrid Reasoning Decision Support System," filed on May 5, 2008, which is herein incorporated by reference in its entirety.

BACKGROUND

1. Field of Disclosure

Aspects of the present invention relate to decision support systems, and more particularly, to decision support systems that employ hybrid rules-based and case-based reasoning.

2. Discussion of Related Art

Decision support systems (DSSs) are typically designed to provide users with near real-time access to complex bodies of knowledge. Often the users of DSSs are themselves experts in the bodies of knowledge at which the DSS is targeted, and these users harness the DSS to better apply their knowledge to a particular set of facts. Thus, conventional DSSs accept a set of facts and, based on these facts and the content of the pertinent body of knowledge, provide potential conclusions drawn from application of the pertinent body of knowledge.

A DSS may be broadly categorized according to how the DSS stores and applies, or reasons with, a body of knowledge. Conventionally, there are at least three such categorizes of DSS reasoning. These categories include rule-based reasoning (RBR), case-based reasoning (CBR) and hybrid RBR/CBR. RBR uses facts derived from a well-constructed domain theory to produce knowledge. In rules-based systems, rules, stored in the form of logical implications, or if/then statements, form the building blocks of the decision making process.

CBR recognizes the power of individual solutions and solves problems by retrieving cases from a database of prior cases and adapting the solutions of the retrieved cases to fit the use case data. In CBR, instead of using general domain knowledge to solve a current case, specific knowledge from previous cases is used. Conventionally, CBR systems share the following cycle:

1. RETRIEVE. The most similar case to the current one is retrieved. In some CBR systems, syntactical similarities are used and in others semantic similarities are used. A commonly used method for case retrieval is neighborhood matching where the case similarity may be computed as shown below, where wi are feature weights, Fi_i is the ith feature in the input case, and Fi_o is the ith features in the retrieved case:

$$\frac{\sum_{i=1}^{n} wiXsim(Fi\_i, Fi\_o)}{\sum_{i=1}^{n} wi}$$

2. REUSE. The information in the most similar case is reused to solve the current case. This reuse may include simply applying the solution of an old case the new case. Reuse may also include adapting, by either reusing the past case solution after a transformation that matches to the current case, or by applying a method used in the solution of the past case.

3. REVISE. The solution is evaluated in the context of the current case and revised appropriately. Often this evaluation is conducted by an expert and may last from a few hours to a few months.

4. RETAIN: The case base is updated with the solution of the current case. In case of success, the case base is updated with the current case and, optionally, index strengths that contributed to the successful solution are strengthened. In case of failure, index strengths that contributed to the failure are weakened.

Conventionally, cases are represented using a variety of data structures. One popular technique is the dynamic memory model, where cases with similar structure are organized in a general structure, known as a generalized episode (GE). A GE contains norms, which are features common to all cases, and indices, which are features that discriminated between cases. Another popular technique is the category and exemplar model, which organizes the cases in a network of categories, semantic relationships, cases, and index pointers.

Conventional case indexing schemes include case indexing by the features with the most predictive power, difference-based indexing and explanation-based generalization methods. When indexing by the features with the most predictive power, features that are responsible for providing a solution to the case are indexed. Difference-based indexing uses indices that differentiate cases from other similar cases. Explanation-based generalization methods form an abstract case from common features and the abstract case is indexed via these common features.

A number of CBR systems have been developed in both industry and academia. These CBR systems include CBR Express/ART-Enterprise from Inference Corporation, which are used primarily for help desk applications, Remind from Cognitive Systems Inc., and ReCall from ISoft. Non-commercial CBR systems for specific applications, such as clinical audiology, heart failure and meal planning, have also been developed.

Hybrid RBR/CBR systems developed in response to the deficiencies of RBR and CBR, when each is applied individually. Systems using this reasoning approach typically marshal reasoning activates between RBR and CBR engines in an attempt to reap the benefits of both.

SUMMARY

According to some aspects of the invention, it is appreciated that in a clinical care environment clinicians are required to make decisions based on partial information and identify salient clues in a maze of clinical data. When available, traditional evidence-based knowledge and standardized guides may support off-line clinical decisions; however, there is a significant need for real-time access to evidence-based knowledge. In addition, despite the fact that modern hospitals are well equipped with patient monitoring and data collection devices, salient patient data, to a large extent, remain unutilized for information extraction purposes related to patient care.

In broad overview, aspects and embodiments disclosed herein provide for a system that overcomes or alleviates some of the problems associated with conventional DSSs and that may identify new knowledge not yet considered in a clinical situation. Embodiments may provide for decision support systems that utilize CBR and RBR to (a) represent patient case bases in a compact way that captures frequency of appearance of both cases and rules, so that information may be harvested efficiently, (b) implement a quality metric for case usefulness, that is based on tracking of case look up and actual case usage in new problems, (c) employ "useful cases" to update the importance of rules in the rule-based engine and (d) employ a similarity metric that encompasses semantic, temporal and quantitative aspects of cases, while also taking into account ontological relationships.

Other embodiments provide for a clinical DSS that utilizes RBR integrated with multi-context CBR. The DSS may be an evidence-based system, and the system may be individualized to a specific patient and integrated with the flow of clinical practice. The system may serve to reduce risk and identify clinical problems in an early stage by minimizing decision errors of omission in situations of clinical uncertainty. The system may be of particular value to the novice clinicians facing an atypical situation in medical-surgical environments.

According to one aspect a method for indexing a plurality of nodes using a computer system in provided. The computer system includes data storage and a processor coupled to the data storage. The method includes acts of storing the plurality of nodes in the data storage, each of the plurality of nodes having a hit count, a link count and an outcome, the hit count of each node indicating a number of times a case attribute associated with the node is presented to a user, the link count of each node indicating a number of times the case attribute associated with the node is affirmed as useful, the outcome of each node indicating a desirability of the outcome, creating a qualitative index ordering a plurality of nodes according to the hit count, the link count and the outcome of each node and storing the qualitative index in the data storage.

In an embodiment, the act of storing the plurality of nodes may include an act of storing a tree of nodes. In addition, the act of storing the plurality of nodes may include an act of storing a plurality of cases. Moreover, the act of storing the plurality of cases may include an act of storing a hit count of each case indicating a number of times a rule associated with the case was presented to the user. Further, the act of creating the qualitative index may include an act of ordering the plurality of nodes in descending order.

In another embodiment, the method may further include acts of creating a semantic index ordering the plurality of nodes according to a diagnosis-related group associated with each node, creating a quantitative index ordering the plurality of nodes according to a plurality of patient data values associated with each node, creating an ontological index ordering the plurality of nodes according to at least one clinical term taxonomy, creating a temporal index ordering the plurality of nodes according to a time period associated with each node and creating a temporal-ontological index ordering the plurality of nodes according to a time period associated with each node and the at least one clinical term taxonomy. In addition, the method may further include acts of receiving a first case from the user, the first case including a patient history, a patient characteristic, a diagnosis and an intervention, determining, using the diagnosis, a semantic similarity between the first case and a plurality of cases associated with at least one of the plurality of nodes, determining, using the patient characteristic and the intervention, a quantitative similarity between the first case and the plurality of cases and determining, using the patient history, a temporal similarity between the first case and the plurality of cases. Moreover, the method may further include acts of determining a similarity vote based at least in part on the semantic similarity, the quantitative similarity and the temporal similarity, the similarity vote indicating a second case of the plurality of cases and presenting the second case to the user. Further, the method may further include acts of adjusting the hit count of any of the plurality of nodes when a case attribute associated with a node is presented to the user and adjusting the link count of any of the plurality of nodes when the case attributed associated with the node is affirmed as useful.

According to another aspect, a system for indexing a plurality of nodes is provided. The system includes a storage medium and a processor coupled to the storage medium. The processor is configured to store the plurality of nodes on the storage medium, each of the plurality of nodes having a hit count, a link count and an outcome, the hit count of each node indicating a number of times a case attribute associated with the node is presented to a user, the link count of each node indicating a number of times the case attribute associated with the node is affirmed as useful, the outcome of each node indicating a desirability of the outcome, create a qualitative index ordering a plurality of nodes according to the hit count, the link count and the outcome of each node and store the qualitative index in the data storage.

According to an embodiment, the processor configured to store the plurality of nodes may be further configured to store a tree of nodes. In addition, the processor configured to store the plurality of nodes may be further configured to store a plurality of cases. Moreover, the processor configured to store the plurality of cases may be further configured to store a hit count of each case indicating a number of times a rule associated with the case was presented to the user. Further, the processor configured to create the qualitative index may be further configured to order the plurality of nodes in descending order.

According to another embodiment, the processor may be further configured to create a semantic index ordering the plurality of nodes according to a diagnosis-related group associated with each node, create a quantitative index ordering the plurality of nodes according to a plurality of patient data values associated with each node, create an ontological index ordering the plurality of nodes according to at least one clinical term taxonomy, create a temporal index ordering the plurality of nodes according to a time period associated with each node and create a temporal-ontological index ordering the plurality of nodes according to a time period associated with each node and the at least one clinical term taxonomy. In addition, the processor may be further configured to receive a first case from the user, the first case including a patient history, a patient characteristic, a diagnosis and an intervention, determine, using the diagnosis, a semantic similarity between the first case and a plurality of cases associated with at least one of the plurality of nodes, determine, using the patient characteristic and the intervention, a quantitative similarity between the first case and the plurality of cases and determine, using the patient history, a temporal similarity between the first case and the plurality of cases. Moreover, the processor may be further configured to determine a similarity vote based at least in part on the semantic similarity, the quantitative similarity and the temporal similarity, the similarity vote indicating a second case of the plurality of cases and present the second case to the user. Further, the processor may be further configured to adjust the hit count of any of the plurality of nodes when a case attribute associated with a node is presented to the user and adjust the link count of any of the plurality of nodes when the case attributed associated with the node is affirmed as useful.

According to another aspect, a system for indexing a plurality of nodes is provided. The system includes a storage medium, a processor coupled to the storage medium and a mechanism for indexing cases under a semantic index, an ontological index, a qualitative index, a quantitative index, a temporal index and a temporal ontological index. In one embodiment, the system may further include means for determining a similarity vote based at least in part on a semantic similarity, an ontological similarity, a qualitative similarity, a quantitative similarity, the temporal similarity and a temporal ontological similarity.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
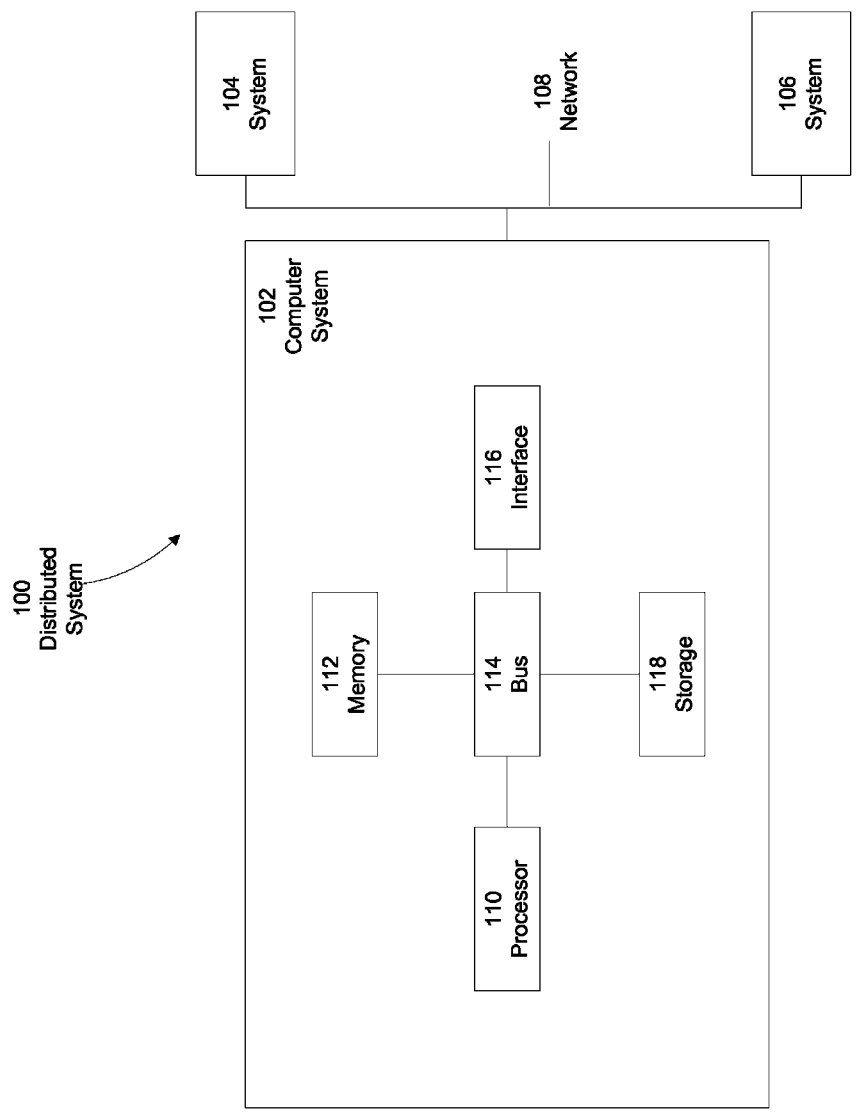
FIG. 1 shows an example computer system with which various aspects in accord with the present invention may be implemented.

As discussed further below according to some aspects of the invention, a DSS is provided for use in a clinical setting. More particularly, embodiments may use software and hardware to assist clinicians in the treatment of patients by presenting treatment options tailored to the patients' situations. In addition, the quality of the match between the patients' situations and the treatment options presented may be honed through feedback collected by previous system usage. Thus, embodiments of the invention may adapt over time to increase the quality of patient care.

While some embodiments disclosed herein are directed toward medical diagnostic and treatment concerns, it is to be appreciated that embodiments of the methods and apparatus discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items.

According to one embodiment, a patient-centric, computer-based clinical decision support tool is provided that combines CBR and RBR to aid the clinician in making clinical decisions. A clinical decision may be an intervention, a diagnosis, or the choice of a specific assessment. A case may include patient facts and clinical decisions. RBR may serve as the primary reasoning mode and CBR may be the auxiliary reasoning mode. The rules used in RBR may be derived from evidence-based practice. A case base, used in CBR, may include individual patient cases, which may conform to, or vary from, established rules. The case base may also include aggregated, merged and/or composite patient cases. The case base may be utilized to support or weaken rules used in RBR, based on the quality of the rule application in similar cases. Cases may also be used along with higher order aggregates, such as criticalness/medical priority, to determine which rule parameters, such patient measurements, must be taken to validate a proposed diagnosis. In addition, this usage of the case base may expose new knowledge by exposing relationships across cases that were never considered before.

Computer System

Various aspects and functions described herein in accord with the present invention may be implemented as hardware or software on one or more computer systems. There are many examples of computer systems currently in use. These examples include, among others, network appliances, personal computers, workstations, mainframes, networked clients, servers, media servers, application servers, database servers and web servers. Other examples of computer systems may include mobile computing devices, such as cellular phones and personal digital assistants, and network equipment, such as load balancers, routers and switches. Further, aspects in accord with the present invention may be located on a single computer system or may be distributed among a plurality of computer systems connected to one or more communications networks.

For example, various aspects and functions may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Consequently, the invention is not limited to executing on any particular system or group of systems. Further, aspects may be implemented in software, hardware or firmware, or any combination thereof. Thus, aspects in accord with the present invention may be implemented within methods, acts, systems, system elements and components using a variety of hardware and software configurations, and the invention is not limited to any particular distributed architecture, network, or communication protocol.

FIG. 1 shows a block diagram of a distributed computer system 100, in which various aspects and functions in accord with the present invention may be practiced. Distributed computer system 100 may include one more computer systems. For example, as illustrated, distributed computer system 100 includes computer systems 102, 104 and 106. As shown, computer systems 102, 104 and 106 are interconnected by, and may exchange data through, communication network 108. Network 108 may include any communication network through which computer systems may exchange data. To exchange data using network 108, computer systems 102, 104 and 106 and network 108 may use various methods, protocols and standards, including, among others, Token Ring, Ethernet, Wireless Ethernet, Bluetooth, TCP/IP, UDP, HTTP, FTP, SNMP, SMS, MMS, SS7, JSON, SOAP, CORBA, REST and Web Services. To ensure data transfer is secure, computer systems 102, 104 and 106 may transmit data via network 108 using a variety of security measures including TSL, SSL or VPN, among other security techniques. While distributed computer system 100 illustrates three networked computer systems, distributed computer system 100 may include any number of computer systems and computing devices, networked using any medium and communication protocol.

Various aspects and functions in accord with the present invention may be implemented as specialized hardware or software executing in one or more computer systems including computer system 102 shown in FIG. 1. As depicted, computer system 102 includes processor 110, memory 112, bus 114, interface 116 and storage 118. Processor 110 may perform a series of instructions that result in manipulated data. Processor 110 may be a commercially available processor such as an Intel Xeon, Itanium, Core, Celeron, Pentium, AMD Opteron, Sun UltraSPARC, IBM Power5+, or IBM mainframe chip, but may be any type of processor, multiprocessor or controller. Processor 110 is connected to other system elements, including one or more memory devices 112, by bus 114.

Memory 112 may be used for storing programs and data during operation of computer system 102. Thus, memory 112 may be a relatively high performance, volatile, random access memory such as a dynamic random access memory (DRAM) or static memory (SRAM). However, memory 112 may include any device for storing data, such as a disk drive or other non-volatile storage device. Various examples in accord with the present invention may organize memory 112 into particularized and, in some cases, unique structures to perform the aspects and functions disclosed herein.

Components of computer system 102 may be coupled by an interconnection element such as bus 114. Bus 114 may include one or more physical busses, for example, busses between components that are integrated within a same machine, but may include any communication coupling between system elements including specialized or standard computing bus technologies such as IDE, SCSI, PCI and InfiniBand. Thus, bus 114 enables communications, for example, data and instructions, to be exchanged between system components of computer system 102.

Computer system 102 also includes one or more interface devices 116 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow computer system 102 to exchange information and communicate with external entities, such as users and other systems.

Storage system 118 may include a computer readable and writeable nonvolatile data storage medium in which instructions are stored that define a program that may be executed by the processor. Storage system 118 also may include information that is recorded, on or in, the medium, and this information may be processed by the processor during execution of the program. More specifically, the information may be stored in one or more data structures specifically configured to conserve storage space or increase data exchange performance. The instructions may be persistently stored as encoded signals, and the instructions may cause a processor to perform any of the functions described herein. The medium may, for example, be optical disk, magnetic disk or flash memory, among others. In operation, the processor or some other controller may cause data to be read from the nonvolatile recording medium into another memory, such as memory 112, that allows for faster access to the information by the processor than does the storage medium included in storage system 118. The memory may be located in storage system 118 or in memory 112, however, processor 110 may manipulate the data within the memory 112, and then copy the data to the medium associated with storage system 118 after processing is completed. A variety of components may manage data movement between the medium and integrated circuit memory element and the invention is not limited thereto. Further, the invention is not limited to a particular memory system or storage system.

Although computer system 102 is shown by way of example as one type of computer system upon which various aspects and functions in accord with the present invention may be practiced, aspects of the invention are not limited to being implemented on the computer system as shown in FIG. 1. Various aspects and functions in accord with the present invention may be practiced on one or more computers having a different architectures or components than that shown in FIG. 1. For instance, computer system 102 may include specially-programmed, special-purpose hardware, such as for example, an application-specific integrated circuit (ASIC) tailored to perform a particular operation disclosed herein. While another example may perform the same function using several general-purpose computing devices running MAC OS System X with Motorola PowerPC processors and several specialized computing devices running proprietary hardware and operating systems.

Computer system 102 may be a computer system including an operating system that manages at least a portion of the hardware elements included in computer system 102. Usually, a processor or controller, such as processor 110, executes an operating system which may be, for example, a Windows-based operating system, such as, Windows NT, Windows 2000 (Windows ME), Windows XP or Windows Vista operating systems, available from the Microsoft Corporation, a MAC OS System X operating system available from Apple Computer, one of many Linux-based operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular implementation.

The processor and operating system together define a computer platform for which application programs in high-level programming languages may be written. These component applications may be executable, intermediate, bytecode or interpreted code which communicates over a communication network, for example, the Internet, using a communication protocol, for example, TCP/IP. Similarly, aspects in accord with the present invention may be implemented using an object-oriented programming language, such as .Net, Small- Talk, Java, C++, Ada, or C# (C-Sharp). Other object-oriented programming languages may also be used. Alternatively, functional, scripting, or logical programming languages may be used.

Additionally, various aspects and functions in accord with the present invention may be implemented in a non-programmed environment, for example, documents created in HTML, XML or other format that, when viewed in a window of a browser program, render aspects of a graphical-user interface or perform other functions. Further, various examples in accord with the present invention may be implemented as programmed or non-programmed elements, or any combination thereof. For example, a web page may be implemented using HTML while a data object called from within the web page may be written in C++. Thus, the invention is not limited to a specific programming language and any suitable programming language could be used.

Examples in accord with the present invention may perform functions outside the scope of the invention. For instance, aspects of the system may be implemented using an existing commercial product, such as, for example, Database Management Systems such as SQL Server available from Microsoft of Seattle Wash., Oracle Database from Oracle of Redwood Shores, Calif., and MySQL from Sun Microsystems of Santa Clara, Calif. or integration software such as Web Sphere middleware from IBM of Armonk, N.Y. However, a computer system running, for example, SQL Server may be able to support both aspects in accord with the present invention and databases for sundry applications not within the scope of the invention.

Example System Architecture

Figure 2:
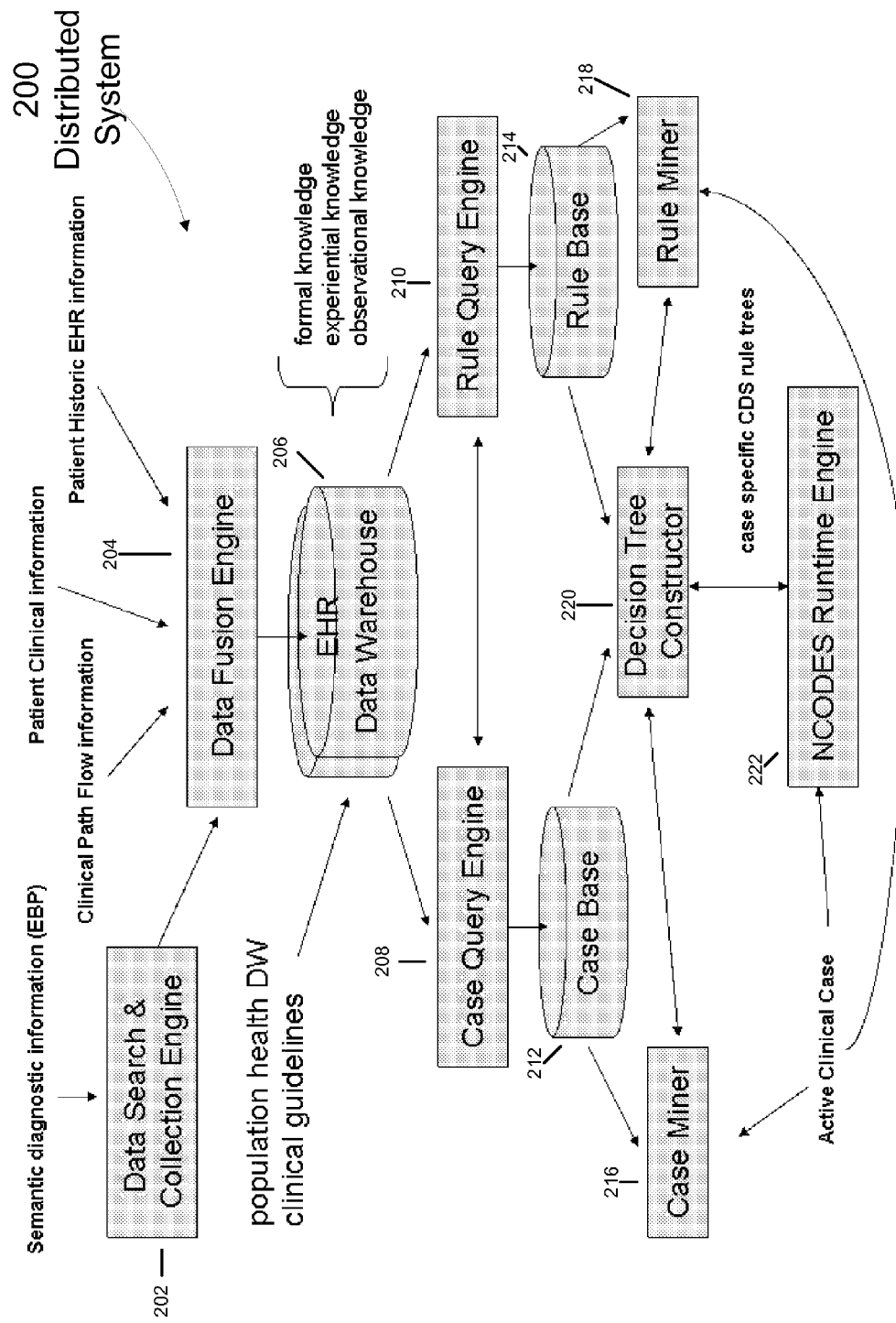
FIG. 2 illustrates a functional block diagram of a system in accord with aspects of the present invention.

FIG. 2 presents a block diagram including physical and logical elements of a distributed system 200. As shown, the distributed system 200 is specially configured in accord of the present invention. The system structure and content recited with regard to FIG. 2 is for exemplary purposes only and is not intended to limit the invention to the specific structure shown in FIG. 2. As will be apparent to one of ordinary skill in the art, many variant system structures can be architected without deviating from the scope of the present invention. The particular arrangement presented in FIG. 2 was chosen to promote clarity.

The distributed systems illustrated by FIG. 2 may include numerous components each of which has a specific function to perform in the context of a patient care episode. As shown, system 200 includes a data search & collection engine 202, a data fusion engine 204, an electronic health record (EHR) data warehouse 206, a case query engine 208, a rule query engine 210, a case base 212, a rule base 214, a case miner 216, a rule miner 218, a decision tree constructor 220 and an NCODES runtime engine 222.

Information may flow between the elements, components and subsystems depicted in FIG. 2 using any technique. Such techniques include, for example, passing the information over the network via TCP/IP, passing the information between modules in memory and passing the information by writing to a file, database, or some other non-volatile storage device. In addition, pointers or other references to information may be transmitted and received in place of, or in addition to, copies of the information. Conversely, the information may be exchanged in place of, or in addition to, pointers or other references to the information. Other techniques and protocols for communicating information may be used without departing from the scope of the invention.

In the embodiment shown, the data search & collection engine 202 receives semantic diagnostic information and provides that information to data fusion engine 204. The data fusion engine 204 receives semantic diagnostic information, clinical path flow information, patient clinical information and patient historic EHR information and provides this information to EHR data warehouse 206. The data fusion engine 204 is described in greater detail below with regard to FIG. 3. The EHR data warehouse 206 houses a variety of information including formal knowledge, experimental knowledge and observational knowledge. The EHR data warehouse 206 provides information to both the case query engine 208 and the rule query engine 210.

In the embodiment shown, the case query engine 208 organizes and indexes this information by case and provides the organized and indexed case information to the case base 212. In a similar fashion, the rule query engine 210 organizes and indexes the information provided by the EHR data warehouse 206 by rule and provides the organized and indexed rule information to the rule base 214. In addition, the case query engine 208 may exchange (i.e. both receive and provide) information with the rule query engine 210.

As depicted by FIG. 2, the case base 212 provides case information to the case miner 216 and the decision tree constructor 220. The rule base 214 provides rule information to the rule miner 218 and the decision tree constructor 220. Both the case miner 216 and the rule miner 218 respectively mine the case base 212 and the rule base 214 for information using a variety of data mining techniques. For instance, according to at least one embodiment illustrated by FIG. 2, the case miner 216 and the rule miner 218 employ, among others techniques, frequency pattern matching.

Frequent pattern (fp) tree building is a technique used in frequency pattern mining of databases. According to frequent pattern tree building, efficiency of mining is achieved by compressing a database of transactions into a compact structure with the most frequent items close to the root of the tree. Under this structure, multiple scans of the database are avoided because when a number of database transactions share an identical set of items, they may be merged into a generalized transaction. This generalized transaction may include an attribute termed a "count" that indicates the number of transactions that share the common item sets.

According to various embodiments illustrated by FIG. 2, the decision tree constructor 220 builds clinical decision support trees. In some embodiments, these trees include frequent case (FC) and frequent rule (FR) trees. Both of these tree types are discussed further below. In addition, the decision tree constructor 220 exchanges information, including decision support trees, with the NCODES runtime engine 222. The NCODES runtime engine supports a variety of client-related data manipulation functions such as receiving active clinical case information and providing a variety of user interfaces to clinicians.

According to various embodiments, system 200 may operate in a client-server configuration, with the server performing computationally significant tasks, such as the functions performed by the data fusion engine 204, the case query engine 208 and the rule query engine 210, and the client performing user data entry and client specific decision support tasks. The engines shown in FIG. 2 provide support for the search, extraction, transformation and fusion of domain knowledge into multiple domain specific ontologies.

Figure 3:
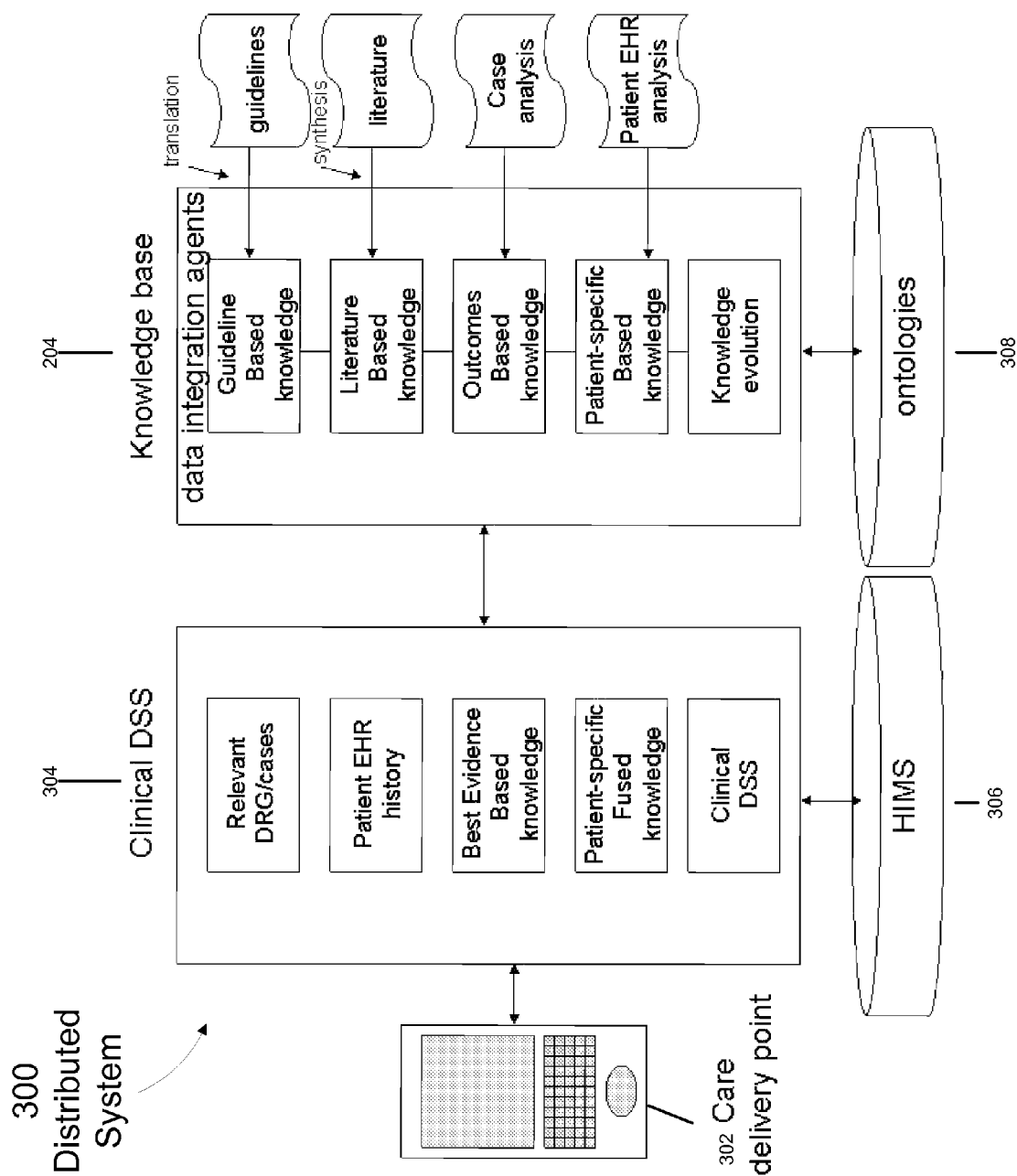
FIG. 3 shows another functional block diagram of a system in accord with aspects of the present invention.

FIG. 3 illustrates another distributed system 300 in accord with the present invention. As shown, distributed system 300 includes a care delivery point 302, which is implemented using a computer system such as a mobile computing device, a clinical DSS 304, a health information management system (HIMS) data warehouse 306, an ontologies database 308 and the data fusion engine 204. In various embodiments, these components utilize the various domain ontologies and root data sources to aid in the transformation process. To build and evolve the knowledge bases, some embodiments may search out new root data sources, such as best evidence guidelines, relevant research literature and available related patient cases and may fuse them with pre-existing and/or new domain ontologies.

In the embodiment shown, the data fusion engine 204 includes several knowledge base data integration agents. These integration agents may include, among other agents, a guideline based knowledge agent, a literature based knowledge agent, an outcomes based knowledge agent, a patient-specific based knowledge agent and a knowledge evolution agent. As illustrated, these integration agents each receive and parse information from a data source and process, in conjunction with the knowledge evolution agent, the data for storage in one or more ontologies included in the ontologies database 308. In the embodiment shown, the data sources that supply data to the integration agents include established medical guidelines, literature, case analysis and patient EHR analysis. Other embodiments may include other integration agents and other data sources without departing from the scope of the present invention.

The ontologies built by the data fusion engine 204 may help to establish a common representation and understanding of domain knowledge from a variety of levels. They may aid in separating domain knowledge from operational knowledge, characterize constraints concerning the use of data objects, establish correspondence, or relationships, between different domains and aid in defining data provenance, pedigree, lineage, relevance, localization, accuracy, and timeliness of extracted information. According to the embodiment shown, the collected, annotated and/or fused information may be stored in a domain data warehouse, referred to in FIG. 3 as the HIMS data warehouse 306, for use within the system.

Figure 4:
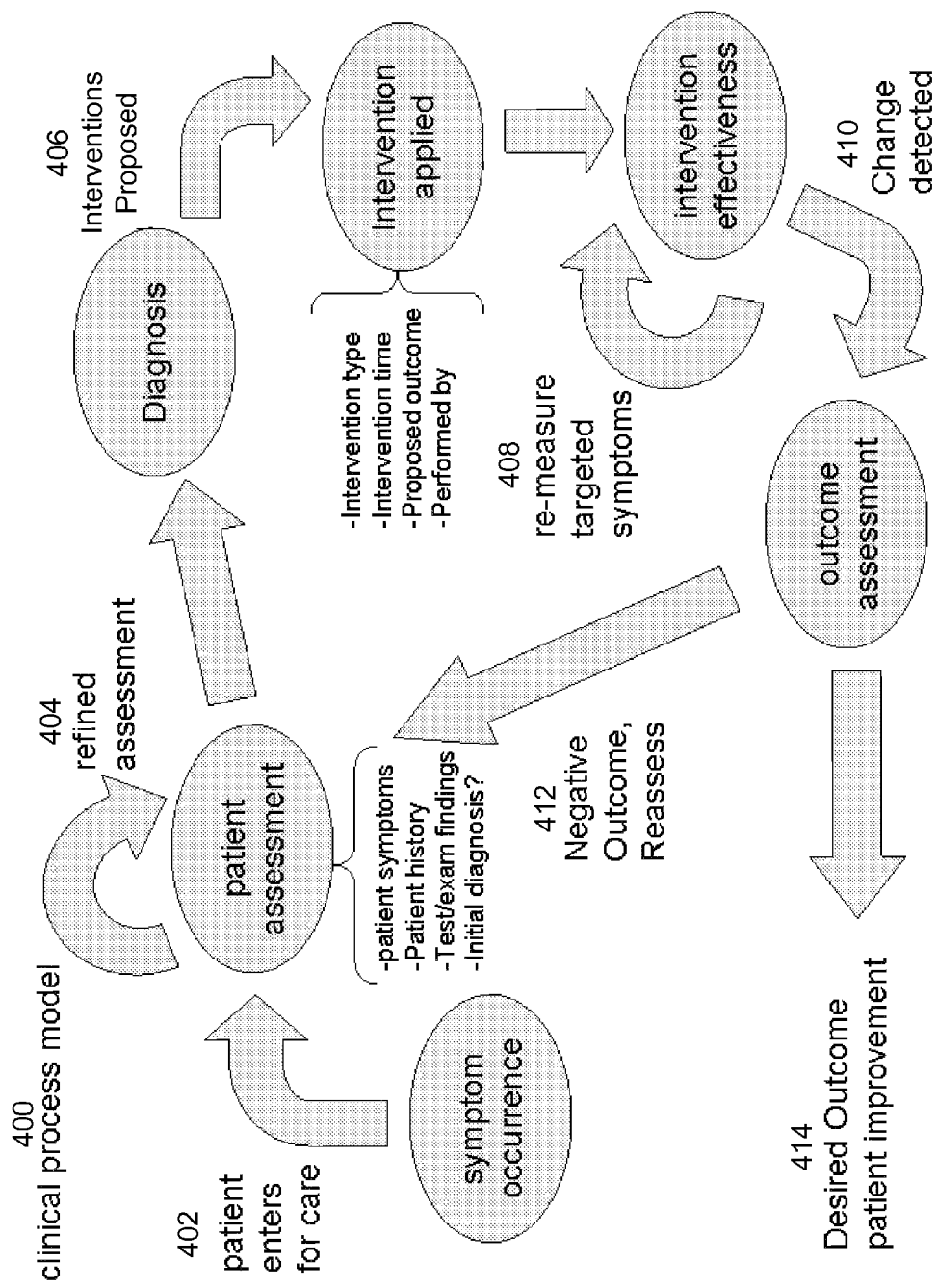
FIG. 4 depicts a process model in accord with aspects of the present invention.

With combined reference to FIGS. 3 and 4, in some embodiments, the HIMS data warehouse 306 may be used by the rule and case query engines 208 and 210 to extract diagnosis related group (DRG) specific information and to construct generic and patient specific cases which may include patient care event sequences. This may be followed by construction of derived case composite rules both generic and patient specific. The results of this phase of operation may be stored into the rule and case bases 214 and 212 in the form of ontology instances for either a rule or an entire case. These stored information elements may then used to build frequent case (FC) and frequent rule (FR) trees which are discussed further below.

The databases 206, 212, 214, 306 and 308 may take the form of any logical construction capable of storing information on a computer readable medium including flat files, indexed files, hierarchical databases, relational databases or object oriented databases. In addition, links, pointers, indicators and other references to data may be stored in place, of or in addition to, actual copies of the data. The data may be modeled using unique and foreign key relationships and indices. The unique and foreign key relationships and indices may be established between the various fields and tables to ensure both data integrity and data interchange performance. Also, according to various embodiments, the databases 206, 212, 214, 306 and 308 may be individual databases or combined into one or more databases. For example, according to one embodiment, the EHR data warehouse 206 and the HIMS data warehouse 306 are incorporated into a single database. Decision Support Processes and Supporting Data Structures FIG. 4 depicts a process model 400 in accord with aspects of the present invention. The depicted process 400 may be performed by an expert clinician for each patient based on the clinician's formal, experiential and observational knowledge. In the embodiments illustrated by FIG. 4, the clinician performs this process with the assistance of the computer-based clinical decision support tool discussed above. In one embodiment, the computer-based clinical decision support tool is implemented using a mobile computing device, such as a PDA or other mobile computing device.

The illustrated clinical process model begins operations in act 402 with a patient's entry into a system based on recognition of symptoms and initial entry by a clinician or other user. In one embodiment, the system may then execute an initial assessment module that, upon detecting a new patient identity, would extract the patient's health history from the knowledge base and the HIMS data warehouse 306. The system may then accept user requests to assess patient symptoms or provide interventions for consideration, if a diagnosis has already been determined During initial assessment the system may use the clinical DSS 304 to query the clinician for measurement and entry of a variety of typical symptoms. Symptoms may be used along with the patient's health history to initiate matching to prior cases including similar symptoms using suitable rules.

Similarity searches may be initiated using various techniques. In one embodiment, rules may be used to search for similar cases following DRG-situated decision trees, where the DRGs are specified by the clinician. There may be two types of such trees: FR trees and FC trees. According to another embodiment, similar cases may be found by following FC trees to the leaves which include DRGs. FR trees, FC trees and FC trees with DRGs included in leaves will be discussed further below. If initial assessment does not produce an acceptable match, further testing and exams may be requested to further refine the possible diagnosis.

In one embodiment, once a refined assessment has been completed in act 404, the system may use past patient history, an ontological stored DRG and case and rule prioritizations, along with stored case and rule instances, to isolate to the most probable diagnosis. Using these diagnoses, salient interventions may be proposed in act 406 along with hypothesized outcomes for the clinician to select based on ontological presented best evidence. Upon intervention selection, the system may wait in act 408 for inputs from intervention symptom measurements to be used in assessing the effectiveness of a selected intervention. Upon completion of intervention assessment, the system may detect changes in act 410 by performing an outcome assessment, which looks to match actual patient symptoms against those of past patients and ontological norms for determination of a positive or negative outcome. If a positive result is found, the case may be added to the data store and data structures, such as FC trees, FR trees and related indices, may be updated in act 412. Likewise, if a negative result is found, data structures and indices may be altered to negatively highlight the case in act 414.

As stated above, according to some embodiments, cases may be represented in FR and FC trees. In these trees, the pathways may be constructed based on the descending frequency of cases or case attributes, such as rules. Attributes of the case may include patient data, such as temperature values, blood pressure values and/or patient symptoms such as chest pain. In an embodiment, the procedure for the construction of the tree may be similar to the construction of an fp tree, as described above. To date, fp trees have not been used for the organization of cases in case-based reasoning, or for iterative growth of frequent patterns. In some embodiments, the case base 212 may be divided in DRGs, and each group may have its own FC tree and FR tree. In addition, there may be FC trees that exist outside a DRG space which are termed non-DRG FC trees.

Figure 5:
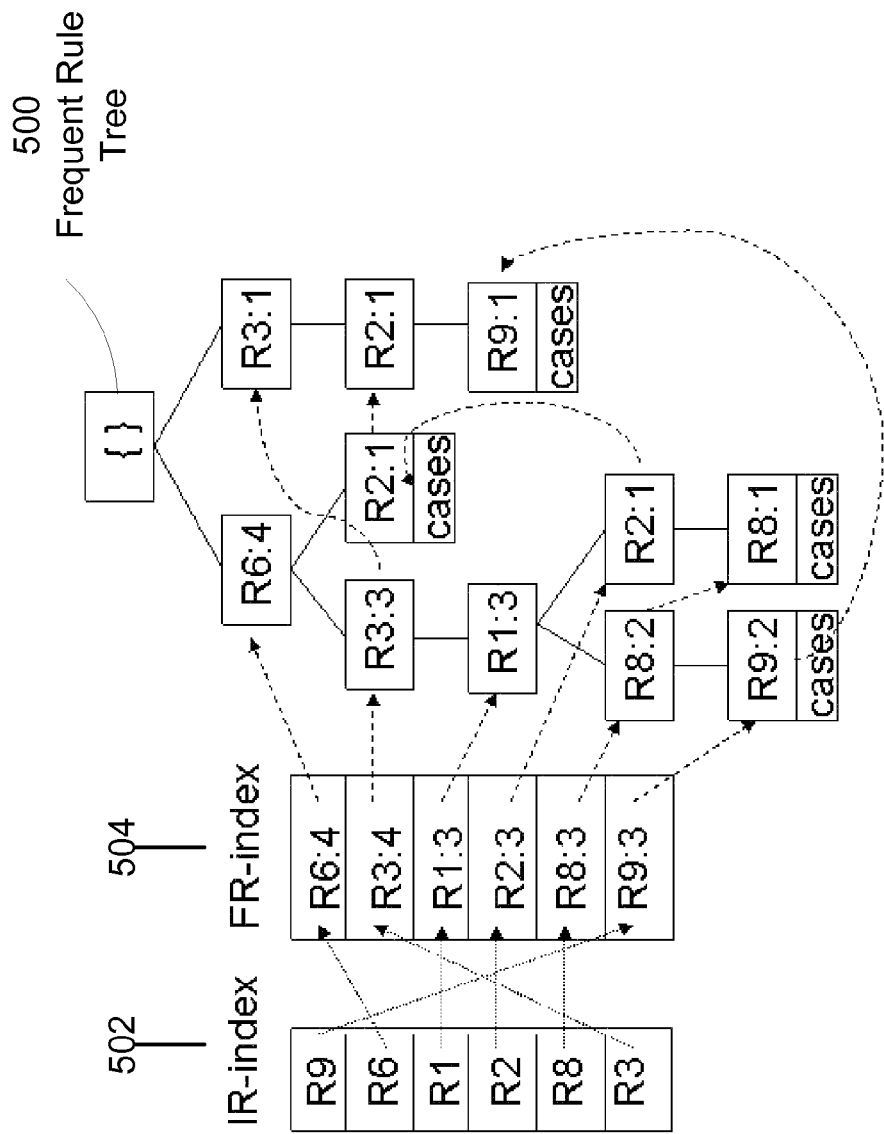
FIG. 5 illustrates a data structure in accord with aspects of the present invention.

Within-DRG FR trees may exist within a DRG. For example, there may be an FR tree for the DRG pneumonia and a separate tree for the DRG emphysema. FIG. 5 illustrates data structures including an FR tree 500 according to various embodiments. In addition, FIG. 5 illustrates the relationship between the FR tree 500 and an IR-index 502 and an FR-index 504. The IR-index 502 orders rules by rule "risk factor" weight, i.e. their ability to confirm or exclude a high risk prognosis. According to some embodiments, the rule risk rate is received from the HIMS data warehouse 306. The FR-index 504 orders rules by frequency of occurrence within the case base 212. In the embodiment shown, the most frequent attributes, such as rules, interventions, and outcome assessments, of DRG1 may be R6(4), R3(4), R1(3), R2(3), R8(3) and R9(3) in that order. The FR tree may be organized as a set of nodes representing the rules encountered during the processing of a given patient care episode, or case. The node counts may represent the number of individual cases which have utilized a specific attribute, such as a rule, in determining the appropriate diagnosis, intervention and outcome sequence. The leaves of the tree may represent one or more instances of a given complete case. The cases may be stored in the database and indices to them may be stored at the leaves.

The cases at the leaf nodes may be positive or negative exemplars of the DRG. For example, a case at the end of the path R3(1), R2(1), R9(1) in FIG. 5 may have all these attributes and exhibit pneumonia or have all these attributes and exhibit another condition such as asthma. According to this embodiment, cases may constitute entries into other DRG trees that the clinician should consider due to the strong similarity of the DRGs.

To aid in discovering which DRG tree to further investigate for similarity, embodiments may store case frequencies and related DRGs as an alternative FC tree. These trees may include merged cases that span many DRGs, and the number of spanned DRGs may decrease as the tree is traversed towards its leaves. The leaves of these trees may include specific DRGs. For example, in such a tree, fever and cough constitute a merged case near the top of the tree.

The aforementioned non-DRG tree may help in the construction of another type of tree, i.e., FC-trees within DRGs. In an embodiment, FC-trees within DRGs may be constructed by identifying which case is most heavily represented in a given DRG, which collection of cases are related within a DRG by traversing the path from root to leaf and/or which sequences of cases for a specific patient(s) show up with regularity. These FC-trees may indicate possible trends to consider for patient care.

Figure 6:
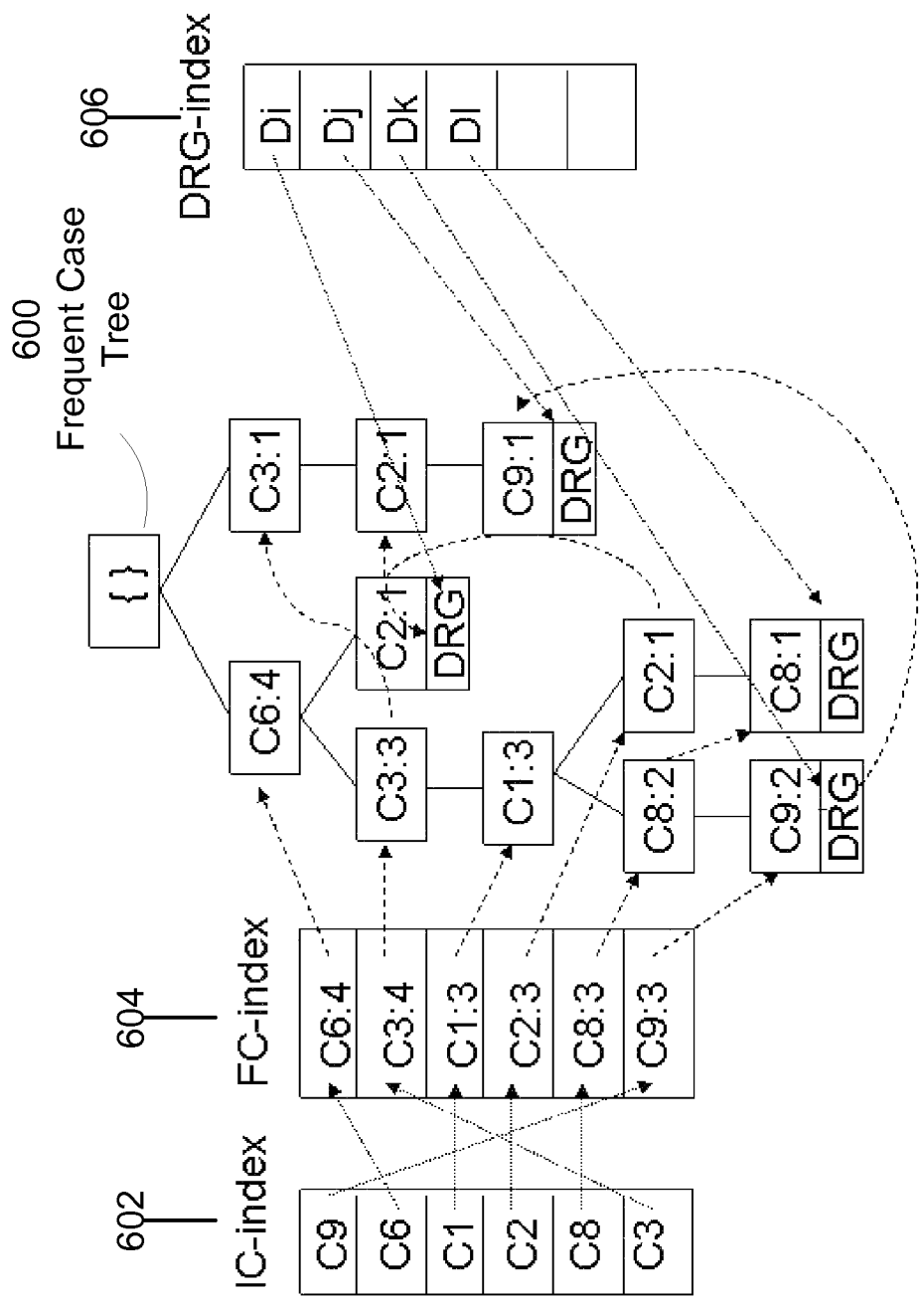
FIG. 6 shows another data structure in accord with aspects of the present invention.

FIG. 6 illustrates data structures including an FC tree 600 according to various embodiments. In addition, FIG. 6 illustrates the relationship between the FC tree 600 and an IC-index 602, an FC-index 604 and a DRG-index 606. The IC-index 602 orders cases by weight with a particular DRG. The FC-index 604 orders cases by frequency of occurrence within the particular DRG. The DRG-index 606 orders DRGs by risk factor weight within all DRGs. According to some embodiments, the orderings of these indices are derived from meta-data stored within the ontologies database 308. The tree 600 illustrated in FIG. 6 represents nodes as case identifiers and the leaves as specific DRGs. In this embodiment, cases may be represented as time sequences of events, such as a path within the related FR-tree, annotated with specific patient and time information.

According to various embodiments, a computer system may perform multi-context case indexing, where a case is indexed under a number of different contexts. These context indices may include, among other indices, semantic, quantitative, temporal, qualitative, ontological, and temporally ontological. Semantic indexing may indicate the DRG that the case belongs to as discussed with regard to FIG. 6 above. Quantitative indexing includes indexing of symptoms and patient data values at the time the case was recorded as discussed with regard to the rule nodes in FIG. 5 above. Both semantic indexing and quantitative indexing are discussed further below.

Ontological indexing may be based on clinical term taxonomies, and it may put a case in different classes, such as a medication class, an interventions class, etc. For example, a case with the Advil medication index may also have the pain reliever ontological index.

Temporal indexing may describe the history for the patient and may include temporal attributes, i.e., attributes with a start and end time that represent temporal events and/or attributes with a single time that represent temporal occurrences. For example, temporal indexing of a case may be: age (date of birth Mar. 9, 1931), heart attack (Jun. 15, 1999), heart-attack-related hospitalization (Jun. 15, 1999 to Jul. 20, 1999), diabetes diagnosed (Sep. 1, 2000), Glucotrol medication (Sep. 1, 2000 to Jun. 5, 2002), severe hypoglycemic episode (Mar. 10, 2001), severe hypoglycemic episode (Mar. 10, 2002), severe hypoglecemic episode (Mar. 10, 2003) and Glucophage medication (June 2002 to present). Temporal indices may be stored as separate dimension table indices on warehoused fact tables. This indexing scheme may allow a system to extract, build and analyze trends for a specific patient related to a new care event.

Temporally ontological indexing may be used to indicate trends and durations of temporal attributes. For example, the above patient history may have the following temporally ontological indexing: (hospitalization that lasted for more than a week), (frequent hypoglecemic episodes), (on Glucophage medication for five years), (Glucotrol medication ended, on it for 2 years). Such data may be stored in the specific EHR for a specific patient, which is part of the EHR data warehouse 206.

Qualitative indexing may indicate how useful the case has been in providing consultation in previous cases. Each case may have a hit count index and a link count index, where a hit means that the case was found similar by the system to an incoming patient case and presented to the user. A link means that the case was affirmed to have actually provided a useful recommendation for an incoming patient case. Each case may also have a quality ranking, Q, which will be a function of the hits, links, and outcome of the case. A potential form of the function is:

$$Q=(\text{sum of links/sum of hits})+\text{Outcome}$$

where Outcome is a numerical indication of the case's outcome. High quality cases include those with a good outcome (for example quick hospital discharge) and with many links. Low quality cases include cases with many hits and a few links. According to one embodiment, the system may also provide link propagation, in the sense that the link count under a specific context of the case gets incremented, if cases that contain its link become links for other cases for the same context.

According to one embodiment, the system may provide for multi-context similarity computation. At the end of the similarity computation process, rules from the top K most similar cases may be displayed to the user, where K is the number that may be configured by the user. The rules may be an intervention, a diagnosis, or need for additional assessment depending on the stage of the patient assessment. The similarity between the current patient case and the retrieved patient cases may be computed under different contexts and presented to the user as the Quality-Controlled Similarity Vote, which is computed as follows:

$$F[\text{Semantic Similarity} + \text{Quantitative Similarity} + \text{Temporal Similarity}, Q]$$

where F is a function of the similarity sum and the quality ranking, Q. For example, if the quality ranking is a number A and the above sum is indicated as S, then a possible function is SA or S×A or S+A. The different types of similarity may be computed as described below.

Semantic similarity may be computed based on the DRG. If the current patient case diagnosis is diabetes, then the case may be considered similar to cases within the diabetes DRG. In the case of multiple simultaneous DRGs such as, for example, diabetes and neuropathy, then the case may be considered similar to cases within the diabetes DRG and cases within the neuropathy DRG. The clinician may indicate on the system, whether diagnosis is determined or not. If the diagnosis of the current case is uncertain, then semantic similarity may not play a role. Semantic similarity may also have an ontological dimension, in the sense that cases that are related taxonomically may also have a degree of similarity in the system. For example, bronchitis and asthma may have a degree of similarity because they both are subclasses of the respiratory disease class.

The next context is quantitative, where embodiments may compute the similarity between individual features of the current case, and features of the retrieved case, with a formula similar to the similarity equation in the background section. Features may include symptoms, such as fatigue or cough, and patient data values, such as high glucose level and temperature, and/or interventions, such as insulin administration. In one embodiment, the weights of the features are based upon their risk factor. Note that the same feature may have a different weight within different DRGs. For example, cough for an otherwise healthy patient with nasal allergies may have a different weight than for a patient with congestive heart failure. If the current patient has a suspected or confirmed DRG, quantitative similarity of the current case may be computed with cases at the leaves of the DRGs FR tree. These leaves may be found at the end of a path that contains the attributes of the current case. As mentioned above, at the leaves of the FR tree, there may be not only cases that belong to this DRG, such as positive exemplars, but also cases that do not belong to this DRG that contain all the attributes of the path. Therefore quantitative similarity may be computed with these cases as well.

Temporal similarity may be computed for cases with a high enough quantitative vote. Temporal similarity may compute the similarity of the current case's patient history and retrieved cases' patient history. Because temporal information is complex, temporal similarity may be guided by the user to look for the right piece of information in the temporal and temporal ontological indices. For example, in a case of a patient where hospitalization is in its 10th day, the clinician may enter "hospitalization duration" to guide the temporal search and the system may retrieve for similarity computation, among others, cases with the temporal ontological index "hospitalization more than a week." In another example, for a diabetic patient currently on Avandia, the user may enter "similar medications in the last three years." The system may use medication ontologies and may bring up histories of patients on Avandia and Actos, which is a similar substance, and may translate the "last 3 years" into a start and end date to obtain the appropriate temporal indices.

In one embodiment, the system may enter the new patient case in the case base, and update the link and hit count of cases that contributed to a clinical decision. Specifically, in one embodiment, a case A may be linked as a contributor to the diagnosis of a new case B, if the following is true: (a) case A is found similar by the system to case B, (b) the diagnosis of case A is presented to the user as a potential choice and (c) a similar diagnosis for case B was confirmed by the user. Similarly, a case A may be linked as a contributor to the choice of an intervention of a new case B, if the following is true: (a) case A is found similar by the system to case B, (b) the intervention of case A is presented to the user as a potential choice for case B and (c) a similar intervention is chosen for case B. Similarity here also may have an ontological dimension. Cases, whose rules were presented to the user, but that did not contribute to the solution of the case, may get an incremented hit count. In addition, the system may indicate in the record of the new case, an identifier of the case that contributed to its solution to allow link propagation in the future.

According to another embodiment, an intelligent agent may be utilized to evolve the case base 212 by performing a process including the following acts among others. The agent may monitor new cases to obtain or update the outcome. The duration of this monitoring activity may range from a few hours to months. The agent may update the frequencies and reorganize the FR and FC trees of the DRG trees as new cases are introduced to the system. The agent may update the indices as new medical information becomes available, such as new medications or temporal constraints, as might be driven by performance demands, for example. The agent may bring to the attention of the clinician, rules, such as choice of specific interventions, that are included in cases with a high hit count and very small or zero link count. This combined with a possible negative outcome may indicate a potentially problematic rule.

Figure 7:
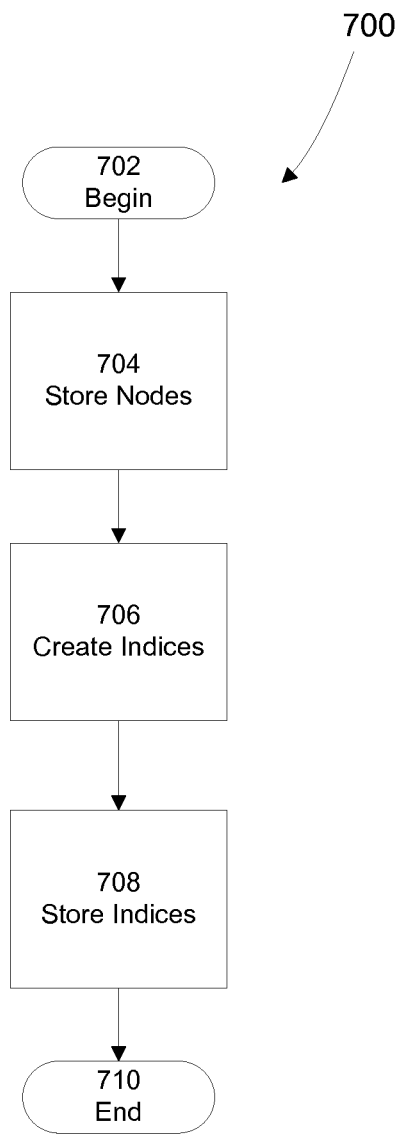
FIG. 7 depicts a process diagram in accord with aspects of the present invention.

Various embodiments provide processes for indexing a plurality of nodes using a computer system. FIG. 7 illustrates one such process 700 that includes acts of storing the nodes in data storage, creating one or more indices and storing the indices in the data storage. Process 700 begins at 702.

In act 704, a computer system stores one or more nodes in data storage. In one embodiment, the computer system that stores the nodes is a computer system arranged and configured in accordance with the distributed system 200, as described above. In this embodiment, the nodes are structured to include a hit count, a link count and an outcome, as described above. In another embodiment, the nodes may include, and be associated with, cases and case attributes, such as rules, also as discussed above. In an additional embodiment, the nodes may be structured as a tree.

In act 706, a computer system creates one or more indices in data storage. In one embodiment, the computer system that creates these indices is a computer system arranged and configured in accordance with the distributed system 200, as described above. In this embodiment, the indices may include a semantic index, a quantitative index, an ontological index, a temporal index and a temporal-ontological index, as described above. In this embodiment, the indices may be based on cases or case attributes associated with the nodes. According to various embodiments, any of these indices may index the nodes in descending order. In an alternative embodiment, any of the indices may index the nodes in ascending order.

In act 708, a computer system stores the indices in data storage. In one embodiment, the computer system that stores the indices is a computer system arranged and configured in accordance with the distributed system 200, as described above.

Process 700 ends at 710.

In some embodiments, process 700 includes additional acts discussed above, such as determining similarities between a case input by a user and one or more of the indices as discussed above. Furthermore, according to some embodiments, process 700 includes acts of presenting historical cases to a user based on a similarity vote, calculated as a function of similarities across several indices, between the input case and the historical cases. In an additional embodiment, process 700 includes acts of adjusting the hit and link count of nodes based on the whether a case is present to, or affirmed by, the user.

Each of process disclosed herein depicts one particular sequence of acts in a particular embodiment. The acts included in each of these processes may be performed by, or using, one or more computer systems specially configured as discussed herein. Thus the acts may be conducted by external entities, such as users or separate computer systems, by internal elements of a system or by a combination of internal elements and external entities. Some acts are optional and, as such, may be omitted in accord with one or more embodiments. Additionally, the order of acts can be altered, or other acts can be added, without departing from the scope of the present invention. As discussed above, in at least some examples, the acts deal with data representative of tangible objects, namely medial patients. In addition, as discussed above, in at least one embodiment, the acts are performed on a particular, specially configured machine, namely a PDA.

It should be appreciated that although aspects and embodiments of the present invention, such as the case indexing and similarity computation are described herein primarily in terms of software, it should be appreciated that they may alternatively be implemented in software, hardware or firmware, or any combination thereof.

Thus, for example, some embodiments of the present invention may comprise any computer-readable medium (e.g., a computer memory, a floppy disk, a compact disk, a tape, etc.) encoded with a computer program (i.e., a plurality of instructions), which, when executed, at least in part, on a processor of a storage system, performs case indexing and similarity computation as described in detail above.

In general summary, aspects and embodiments of the invention thus include a DSS and methods to improve the application of a body of medical knowledge, such as nursing knowledge, to a given situation. However, it should be appreciated that various aspects of the present invention may be used for other purposes. For example, aspects of the present invention may be used to diagnose computer related problems or provide for a system that helps attorneys counsel clients.

Any reference to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements.

Any embodiment disclosed herein may be combined with any other embodiment, and references to "an embodiment," "some embodiments," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment in any manner consistent with the aspects disclosed herein. References to "or" may be construed as inclusive so that any terms described using "or" may indicate any of a single, more than one, and all of the described terms.

Where technical features in the drawings, detailed description or any claim are followed by references signs, the reference signs have been included for the sole purpose of increasing the intelligibility of the drawings, detailed description, and claims. Accordingly, neither the reference signs nor their absence are intended to have any limiting effect on the scope of any claim elements.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A method for indexing a plurality of nodes using a computer system, the computer system including data storage and a processor coupled to the data storage, the method comprising:

storing the plurality of nodes in the data storage, each of the plurality of nodes having a hit count, a link count and an outcome, the hit count of each node indicating a number of times a case attribute associated with the node is presented to a user, the link count of each node indicating a number of times the case attribute associated with the node is affirmed as useful, the outcome of each node indicating a desirability of the outcome;

creating a qualitative index ordering the plurality of nodes according to the hit count, the link count and the outcome of each node; and storing the qualitative index in the data storage, wherein storing the plurality of nodes includes storing a plurality of cases, and wherein storing the plurality of cases includes storing a hit count of each case indicating a number of times a rule associated with the case was presented to the user.

2. The method according to claim 1, wherein storing the plurality of nodes includes storing a tree of nodes.

3. The method according to claim 1, wherein creating the qualitative index includes ordering the plurality of nodes in descending order.

4. The method according to claim 1, further comprising:

creating a semantic index ordering the plurality of nodes according to a diagnosis-related group associated with each node;

creating a quantitative index ordering the plurality of nodes according to a plurality of patient data values associated with each node;

creating an ontological index ordering the plurality of nodes according to at least one clinical term taxonomy;

creating a temporal index ordering the plurality of nodes according to a time period associated with each node;

19 creating a temporal-ontological index ordering the plurality of nodes according to a time period associated with each node and the at least one clinical term taxonomy; and storing the semantic index in the data storage.

5. The method according to claim 4, further comprising:

receiving a first case from the user, the first case including a patient history, a patient characteristic, a diagnosis and an intervention;

determining, using the diagnosis, a semantic similarity between the first case and a plurality of cases associated with at least one of the plurality of nodes;

determining, using the patient characteristic and the intervention, a quantitative similarity between the first case and the plurality of cases; and determining, using the patient history, a temporal similarity between the first case and the plurality of cases.

6. The method according to claim 5, further comprising:

determining a similarity vote based at least in part on the semantic similarity, the quantitative similarity and the temporal similarity, the similarity vote indicating a second case of the plurality of cases; and presenting the second case to the user.

7. The method according to claim 6, further comprising:

adjusting the hit count of any of the plurality of nodes when a case attribute associated with a node is presented to the user; and adjusting the link count of any of the plurality of nodes when the case attribute associated with the node is affirmed as useful.

8. A system for indexing a plurality of nodes comprising:

a storage medium; and a processor coupled to the storage medium and configured to:

store the plurality of nodes on the storage medium, each of the plurality of nodes having a hit count, a link count and an outcome, the hit count of each node indicating a number of times a case attribute associated with the node is presented to a user, the link count of each node indicating a number of times the case attribute associated with the node is affirmed as useful, the outcome of each node indicating a desirability of the outcome;

create a qualitative index ordering the plurality of nodes according to the hit count, the link count and the outcome of each node; and store the qualitative index in the data storage, wherein the processor configured to store the plurality of nodes is further configured to store a plurality of cases, and wherein the processor configured to store the plurality of cases is further configured to store a hit count of each case indicating a number of times a rule associated with the case was presented to the user.

9. The system according to claim 8, wherein the processor configured to store the plurality of nodes is further configured to store a tree of nodes.

10. The system according to claim 8, wherein the processor configured to create the qualitative index is further configured to order the plurality of nodes in descending order.

11. The system according to claim 8, wherein the processor is further configured to:

create a semantic index ordering the plurality of nodes according to a diagnosis-related group associated with each node;

20 create a quantitative index ordering the plurality of nodes according to a plurality of patient data values associated with each node;

create an ontological index ordering the plurality of nodes according to at least one clinical term taxonomy;

create a temporal index ordering the plurality of nodes according to a time period associated with each node;

create a temporal-ontological index ordering the plurality of nodes according to a time period associated with each node and the at least one clinical term taxonomy; and store the semantic index in the data storage.

12. The system according to claim 11, wherein the processor is further configured to:

receive a first case from the user, the first case including a patient history, a patient characteristic, a diagnosis and an intervention;

determine, using the diagnosis, a semantic similarity between the first case and a plurality of cases associated with at least one of the plurality of nodes;

determine, using the patient characteristic and the intervention, a quantitative similarity between the first case and the plurality of cases; and determine, using the patient history, a temporal similarity between the first case and the plurality of cases.

13. The system according to claim 12, wherein the processor is further configured to:

determine a similarity vote based at least in part on the semantic similarity, the quantitative similarity and the temporal similarity, the similarity vote indicating a second case of the plurality of cases; and present the second case to the user.

14. The system according to claim 13, wherein the processor is further configured to:

adjust the hit count of any of the plurality of nodes when a case attribute associated with a node is presented to the user; and adjust the link count of any of the plurality of nodes when the case attribute associated with the node is affirmed as useful.

15. A non-transitory computer readable medium storing sequences of instruction for indexing a plurality of nodes, the sequences of instruction including instructions that instruct at least one processor to:

store the plurality of nodes in the data storage, each of the plurality of nodes having a hit count, a link count and an outcome, the hit count of each node indicating a number of times a case attribute associated with the node is presented to a user, the link count of each node indicating a number of times the case attribute associated with the node is affirmed as useful, the outcome of each node indicating a desirability of the outcome;

create a qualitative index ordering the plurality of nodes according to the hit count, the link count and the outcome of each node; and store the qualitative index in the data storage, wherein the instructions to store the plurality of nodes include instructions to store a plurality of cases, and wherein the instructions to store the plurality of cases include instructions to store a hit count of each case indicating a number of times a rule associated with the case was presented to the user.

* * * * *

UNITED STATES PATENT AND TRADEMARK OFFICE
CERTIFICATE OF CORRECTION

| | | |
|---|---|---|
| PATENT NO. | : 8,504,514 B2 | Page 1 of 1 |
| APPLICATION NO. | : 13/584380 | |
| DATED | : August 6, 2013 | |
| INVENTOR(S) | : Paul J. Fortier et al. | |

It is certified that error appears in the above-identified patent and that said Letters Patent is hereby corrected as shown below:

In the Specification, beginning at line 10, insert the following:

-- FEDERALLY SPONSORED RESEARCH

This invention was made with government support under Grant Number EIA 0218909 awarded by the National Science Foundation. The government has certain rights in the invention. --

Signed and Sealed this
Twenty-eighth Day of July, 2015

Michelle K. Lee
*Director of the United States Patent and Trademark Office*